US00PP30937P3

(12) United States Plant Patent
Jackson

(10) Patent No.: US PP30,937 P3
(45) Date of Patent: Oct. 15, 2019

(54) HOP PLANT NAMED 'J-007'

(50) Latin Name: *Humulus lupulus*
Varietal Denomination: J-007

(71) Applicant: JACKSON HOP, LLC, Caldwell, ID (US)

(72) Inventor: Nathan Jackson, Caldwell, ID (US)

(73) Assignee: JACKSON HOP, LLC, Caldwell, ID (US)

( * ) Notice: Subject to any disclaimer, the term of this patent is extended or adjusted under 35 U.S.C. 154(b) by 55 days.

(21) Appl. No.: 15/530,713

(22) Filed: Feb. 16, 2017

(65) Prior Publication Data

US 2018/0235128 P1 Aug. 16, 2018

(51) Int. Cl.
*A01H 5/00* (2018.01)
*A01H 6/00* (2018.01)
*A01H 5/02* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./226, 236
See application file for complete search history.

*Primary Examiner* — Susan McCormick Ewoldt
*Assistant Examiner* — Karen M Redden
(74) *Attorney, Agent, or Firm* — Ballew Law

(57) ABSTRACT

A new hop plant named 'J-007' is disclosed. 'J-007' is characterized principally as to having a unique aroma, resistance to powdery mildew, compact laterals with a prolific cone set, and above average yield as compared with other aroma varieties.

4 Drawing Sheets

Genus and species: *Humulus lupulus*.
Variety denomination: 'J-007'.

CROSS-REFERENCE TO RELATED APPLICATIONS

None

STATEMENT REGARDING FEDERALLY SPONSORED RESEARCH OR DEVELOPMENT

None

BACKGROUND OF THE INVENTION

'J-007' is a product of a controlled breeding program carried out by the inventor in the Treasure Valley in the State of Idaho. 'J-007' was one of several seedlings resulting from a controlled pollination cross in 2009 between female 'Toyamadori' (non patented in the United States) and a proprietary male hop plant owned by the inventor. A single plant of 'J-007' was identified in 2011, and observed during the growing seasons in 2012 and 2013. In 2014 that single plant of 'J-007' was asexually propagated by softwood cuttings, into a large scale test plot near Wilder, Id. for further observation and evaluation in 2015 and 2016. An evaluation of that test plot shows that 'J-007' has been observed to retain its distinctive characteristics after asexual propagation, and has remained true to type.

BRIEF DESCRIPTION OF THE PHOTOGRAPHS

Figure 1:
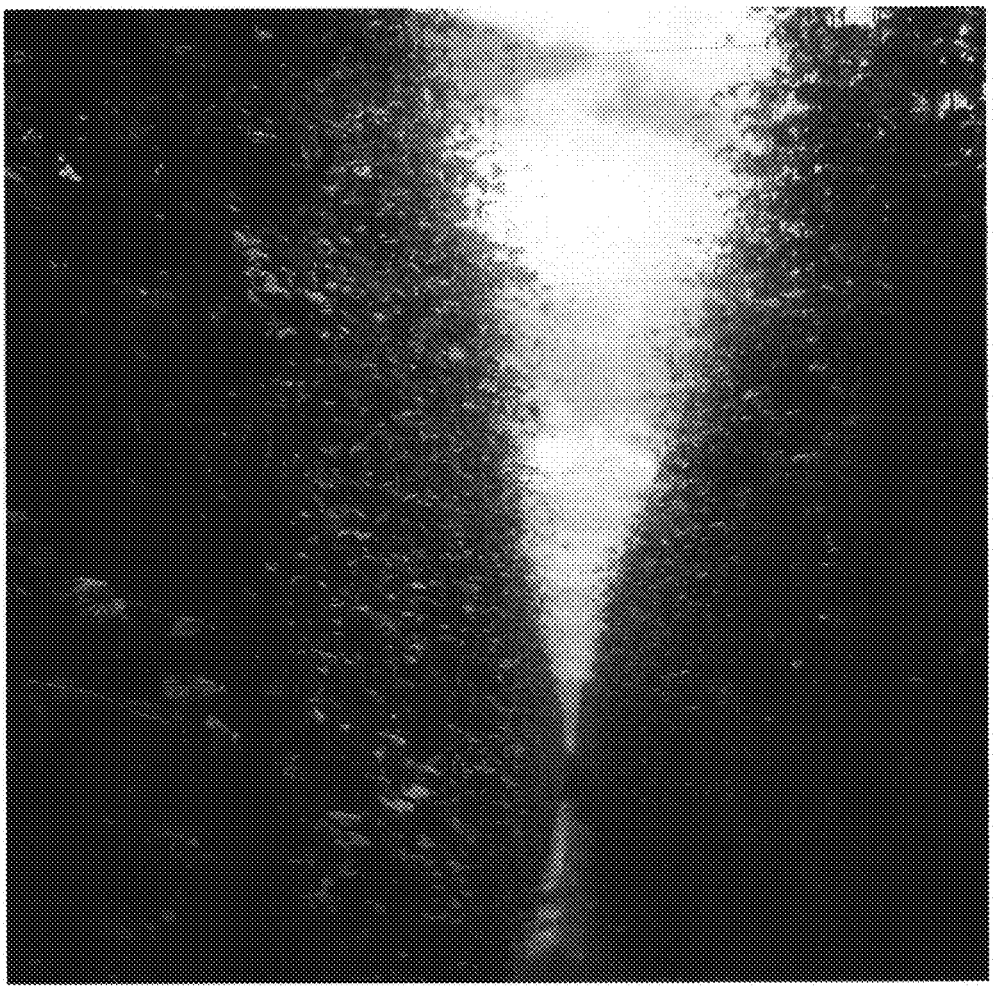
FIG. 1 illustrates two rows of mature 'J-007' hop plant grown on a 18" trellis during late August.
Figure 2:
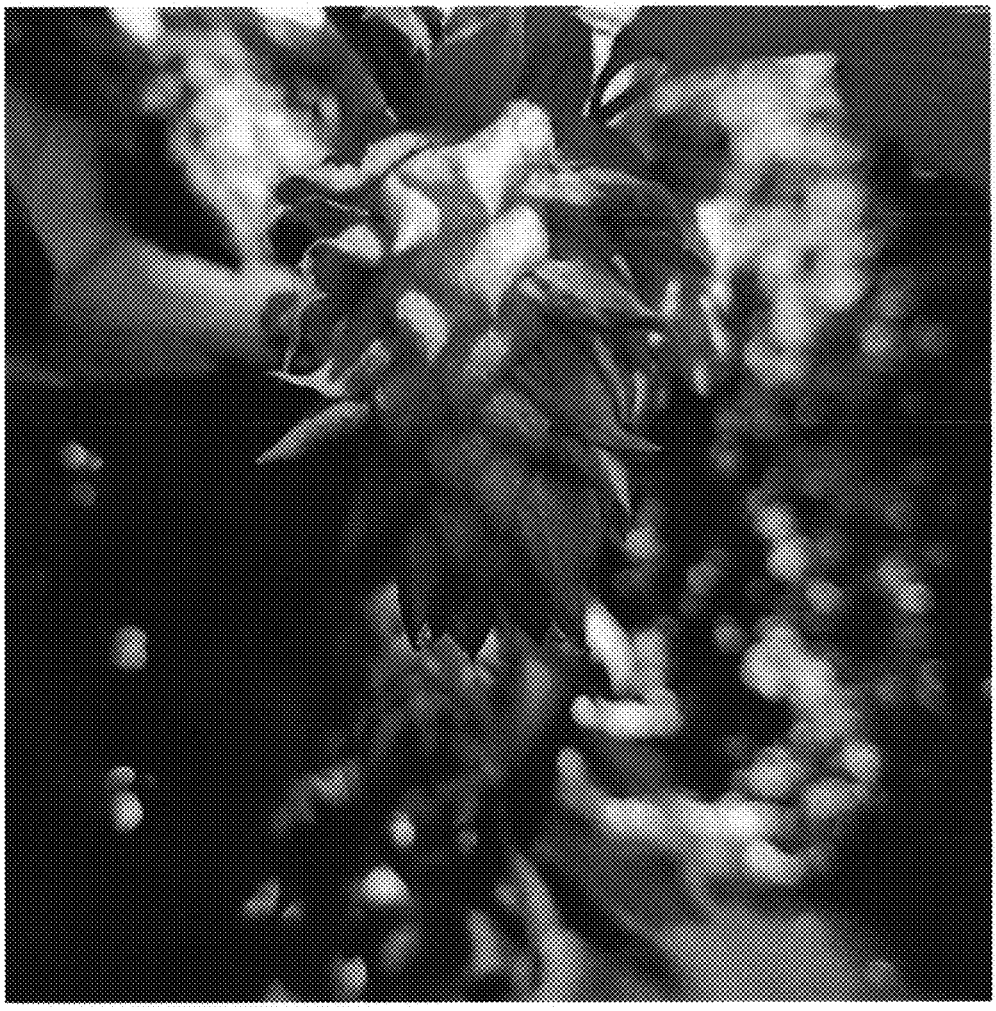
FIG. 2 illustrates a single cone growing on a 'J-007' hop plant during early September.
Figure 3:
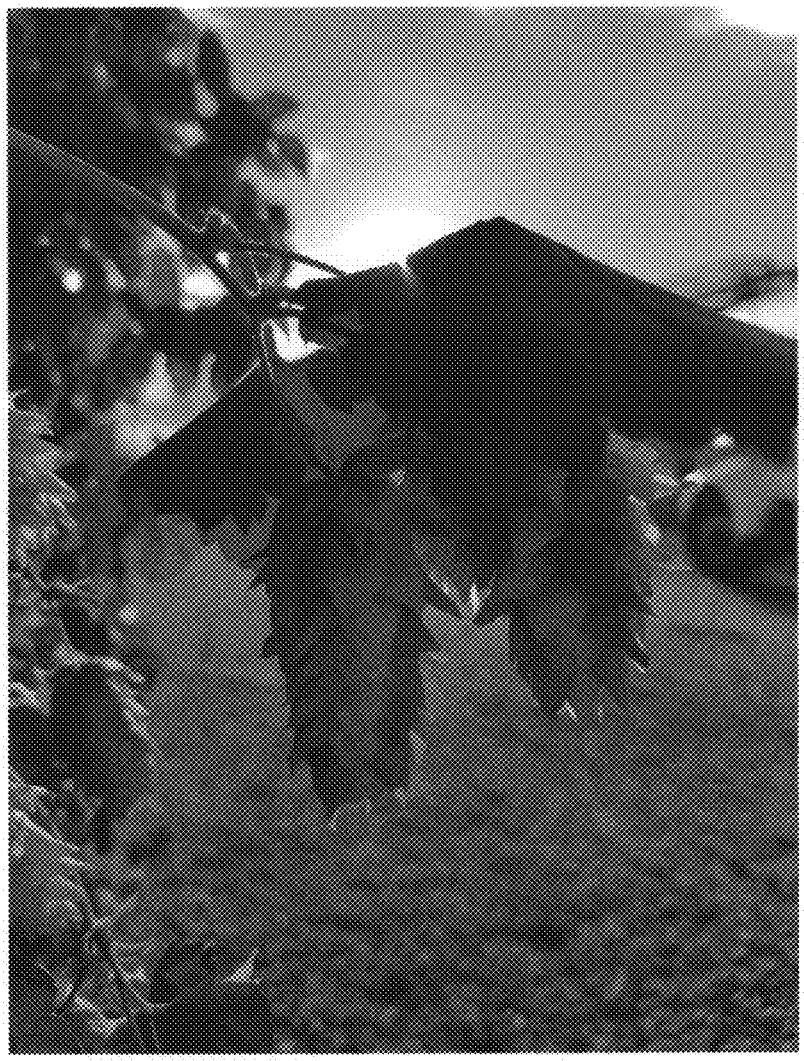
FIG. 3 illustrates the cones and leaves of a mature 'J-007' hop plant during harvest in late September.
Figure 4:
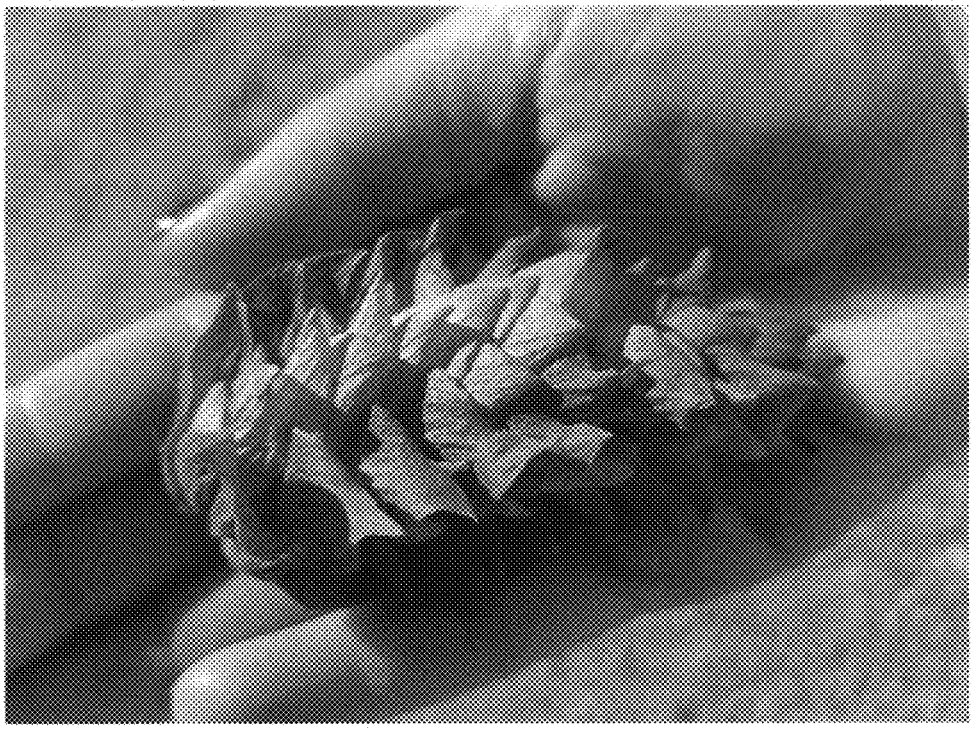
FIG. 4 illustrates a single mature whole cone of 'J-007' hop plant in late September.

The colors of these illustrations may vary with lighting conditions and, therefore, color characteristics of this new variety should be determined with reference to the observations described herein, rather than from these illustrations alone.

DETAILED BOTANICAL DESCRIPTION

The following descriptions are based on observations made at harvest time (September 20-30$^{th}$) during 2015 and 2016 in Wilder, Id.

Table 1. sets forth some of the distinguishing characteristics of 'J007' as compared to its female parent 'Toyamadori' (non patented in the United States) and the 'Summit' variety (patented: U.S. Plant Pat. No. 24,299P2):

TABLE 1

| Characteristic | 'Toyamadori' | 'J-007' | 'Summit' |
|---|---|---|---|
| Alpha Acid (α-Acids, % db) | 12.2 ± 0.6 | 12-14 | 18-19 |
| Beta Acids (β-Fraction, % db) | 7.2 ± 0.3 | 4.0-5.5 | 3.3-4.3 |
| Total Oil (ml/100 g) | 0.69 ± 0.19 | 1.2-2.4 | 1.5 |
| Myrcene (% of Total Oil) | 27 ± 5 | 46-58 | 48.5 |

It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. The color chart used was The Royal Horticultural Society Colour Chart, 5th Edition. All color observations were made outdoors in full sunlight.

Ploidy: Diploid.

Use: Brewing beer.

Harvest date: September 20 to 30 during the 2015 and 2016 growing seasons, Wilder, Id.

Crop yield: 2300 to 2400 pounds per acre.

Disease susceptibility: Tolerant of hop downy mildew, powdery mildew, verticillium wilt, and the virus diseases known to *Humulus lupulus* found in U.S. hop growing areas.

Pest susceptibility: Average susceptibility to pests, including hop aphids and two spotted spider mites.

Plant shape: Fusiform to Columnar when grown on a commercial hop trellis.

Bine:

*Bine color*.—Yellow Green 145A.
*Bine stripe*.—Present.
*Bine stripe color*.—Purple N77D.
*Bine internode length* (*at* 180 *cm* (6') *high above the ground*).—20-25 cm.
*Bine diameter* (*at* 180 *cm high* (6').—12 mm to 14 mm.
*Bine average length*.—487 cm to 580 cm (16' to 19').
*Bine texture*.—Fine, rough hair present; 2-3 cm long. Hair appears to lessen as bine matures and thicken.

Leaf:

*Leaf arrangement*.—Opposite.
*Leaf shape*.—Cordate.
*Mature leaf avg width*.—18 cm.
*Mature leaf avg length*.—16.5 cm.
*Leaf color, mature leaf upper surface*.—Green N137B.
*Leaf color, mature leaf lower surface*.—Green 147B.
*Number of leaf lobes*.—3 to 5.
*Leaf venation*.—Netted (palmately veined).
*Leaf vein color*.—Yellow Green 144B.
*Leaf margin*.—Moderately Dentate.
*Leaf texture*.—Underside: smooth with fine hair and distinct veins. Topside: veined and rough.

Petioles:

*Petiole avg length*.—7 to 8 cm.
*Petiole diameter*.—3 mm to 4 mm.
*Petiole color*.—Green 143B.
*Petiole shape*.—Channeled upper surface.

Laterals:

*Lateral avg length* (*at* 180 *cm* (6') *high from the ground*).—30 cm to 50 cm.
*Avg length of lateral internodes* (*at* 180 *cm* (6') *high*).—9 cm to 11 cm.
*Stipule position*.—Downward.
*Stipule color*.—Green 145B.

Female flowers: Emerge during July (are non distinct for this variety), developing into cones during August and maturing during September.

Cones:

*Shape*.—Ovoid to Elongated.
*Cone avg length*.—4.5 cm to 5.0 cm.
*Cone avg diameter at shoulder*.—2.0 cm to 2.5 cm.
*Cone avg weight*.—250 mg to 320 mg.
*Compactness*.—Moderately firm.
*Cone tip shape*.—Tapered to a fairly distinct point.
*Strig*.—Large with prominent pedicels.
*Lupulin gland color*.—Yellow 2A (not distinctive of this variety).
*Lupulin gland shape*.—Pedunculated oblong polyps.
*Aroma*.—Apricot, nectarine, orange, and black tea.

Bracts:

*Bract tip shape*.—Acute to acuminate.
*Bract tip position*.—Mostly appressed with some bracts being slightly everted.
*Bract diameter*.—13 mm to 14 mm.
*Bract color*.—Green 143A.

Bracteoles:

*Bracteole diameter*.—9 mm to 10 mm.
*Bracteole shape*.—Lanceolate.
*Bracteole color*.—Green 143C.

Analytical characteristics:

*Alpha acid*.—12 to 14%.
*Beta acid*.—4.0 to 5.5%.
*Cohumulone*.—38 to 40% of alpha acids.
*Humulene*.—10 to 15% of total oils.
*Caryophyllene*.—4 to 8% of total oils.
*Myrcene*.—46 to 55% of total oils.
*Farnesene*.—<1% of total oils.
*Total oil*.—1.2 to 2.4 ml/100 g.
*Hop storage index* (*HSI*).—The cones of the present variety experience a 30% to 40% transformation of alpha acids after about 6 months of storage at 22° C.

The invention claimed is:

1. What is claimed is a new and distinct hop plant as shown and described herein.

* * * * *